(12) United States Patent
Borsdorf et al.

(10) Patent No.: US 11,423,554 B2
(45) Date of Patent: Aug. 23, 2022

(54) REGISTERING A TWO-DIMENSIONAL IMAGE WITH A THREE-DIMENSIONAL IMAGE

(71) Applicant: Siemens Healthcare GmbH, Erlangen (DE)

(72) Inventors: Anja Borsdorf, Adelsdorf (DE); Roman Schaffert, Erlangen (DE); Jian Wang, Forchheim (DE); Markus Weiss, Wiesau (DE)

(73) Assignee: Siemens Healthcare GmbH, Erlangen (DE)

( * ) Notice: Subject to any disclaimer, the term of this patent is extended or adjusted under 35 U.S.C. 154(b) by 176 days.

(21) Appl. No.: 16/994,943

(22) Filed: Aug. 17, 2020

(65) Prior Publication Data
US 2021/0065388 A1  Mar. 4, 2021

(30) Foreign Application Priority Data

Aug. 28, 2019 (DE) .......................... 102019212929.3

(51) Int. Cl.
*G06T 7/33* (2017.01)
*G06T 7/00* (2017.01)
*A61B 6/03* (2006.01)

(52) U.S. Cl.
CPC ................ *G06T 7/33* (2017.01); *A61B 6/032* (2013.01); *G06T 7/0012* (2013.01);
(Continued)

(58) Field of Classification Search
CPC ............. G06T 7/33; G06T 2207/10104; G06T 2207/30012; G06T 2207/10088;
(Continued)

(56) References Cited

U.S. PATENT DOCUMENTS

2016/0012592 A1* 1/2016 Chou ........................ G06T 7/35
382/131
2016/0335777 A1 11/2016 Borsdorf
2017/0024634 A1* 1/2017 Miao ........................ G06T 7/33

FOREIGN PATENT DOCUMENTS

DE          102015208929 B3    6/2016

OTHER PUBLICATIONS

Fischer, Philipp, et al. "Flownet: Learning optical flow with convolutional networks." arXiv preprint arXiv:1504.06852 (2015). pp. 1-13.
(Continued)

*Primary Examiner* — Siamak Harandi
(74) *Attorney, Agent, or Firm* — Lempia Summerfield Katz LLC

(57) ABSTRACT

The disclosure relates to a computer-implemented method for the provision of a transformation instruction for registering a 2D image with a 3D image. The method includes: receiving the 2D image and the 3D image; generating input data based on the 2D image having contour pixels and the 3D image having contour voxels; applying a trained function to the input data for identification of contour pixels of the 2D image and contour voxels of the 3D image, wherein at least one parameter of the trained function is adjusted based on a comparison of training contour pixels with comparison contour pixels and a comparison of training contour voxels corresponding thereto with comparison contour voxels; determining the transformation instruction based on the identified contour pixels of the 2D image and the contour voxels corresponding thereto of the 3D image for registering the 2D image with the 3D image; and providing the transformation instruction.

15 Claims, 7 Drawing Sheets

(52) U.S. Cl.
CPC .............. *G06T 2207/10081* (2013.01); *G06T 2207/10088* (2013.01); *G06T 2207/10116* (2013.01)

(58) Field of Classification Search
CPC . G06T 2207/10081; G06T 2207/10116; G06T 2207/20221
See application file for complete search history.

(56) References Cited

OTHER PUBLICATIONS

German Office Action for German Application No. DE 10 2019 212 929.3 dated May 11, 2020.
Wang, Jian, et al. "Dynamic 2-D/3-D rigid registration framework using point-to-plane correspondence model." IEEE transactions on medical imaging 36.9 (2017): 1939-1954.

* cited by examiner

REGISTERING A TWO-DIMENSIONAL IMAGE WITH A THREE-DIMENSIONAL IMAGE

The present patent document claims the benefit of German Patent Application No. 10 2019 212 929.3, filed Aug. 28, 2019, which is hereby incorporated by reference.

TECHNICAL FIELD

The disclosure relates to a computer-implemented method for the provision of a transformation instruction for registering a two-dimensional (2D) image with a three-dimensional (3D) image, a computer-implemented method for registering a 2D image with a 3D image, a computer-implemented method for the provision of a trained function, a training unit, a processing unit, a medical imaging device, a computer program product, and a computer-readable storage medium.

BACKGROUND

In imaging-led interventions, medical X-ray devices, (e.g., medical C-arm X-ray devices), may be used for real-time monitoring of the intervention. Furthermore, the two-dimensional (2D) fluoroscopy images recorded in the process may be overlaid with three-dimensional (3D) volume images, which were preoperatively recorded, (e.g., by a magnetic resonance system (MRT) and/or a computed tomography system (CT) and/or a medical X-ray device). The 2D-3D registering is frequently carried out for this at the beginning of the intervention in order to be able to achieve an optimally high initial accuracy in the 2D-3D registering. The 2D-3D registering may deteriorate during the intervention, in particular, owing to movement of the patient.

In particular, large initial differences between the preoperative 3D volume image and the 2D fluoroscopy image may be disadvantageous to the accuracy of 2D-3D registering. The approaches known from the prior art for improving a robustness of 2D-3D registering, (e.g., consideration of different image resolutions and/or recording of a plurality of fluoroscopy images from different perspectives and/or start positions), may adversely lead to increased computing effort and increased exposure to X-rays for the patient.

SUMMARY AND DESCRIPTION

The disclosure is therefore based on the object of enabling particularly reliable and accurate registering of 2D images with 3D images.

The object is achieved by a computer-implemented method for the provision of a transformation instruction for registering a 2D image with a 3D image, a computer-implemented method for registering a 2D image with a 3D image, a computer-implemented method for the provision of a trained function, a training unit, a processing unit, a medical imaging device, a computer program product, and a computer-readable storage medium as described herein. The scope of the present disclosure is defined solely by the appended claims and is not affected to any degree by the statements within this summary. The present embodiments may obviate one or more of the drawbacks or limitations in the related art.

The solution to the object will be described below both in relation to methods and apparatuses for the provision of a transformation instruction for registering a 2D image with a 3D image and in relation to methods and apparatuses for the provision of trained functions. Features and alternative embodiments of data structures and/or functions in the case of methods and apparatuses for the provision of a transformation instruction for registering a 2D image with a 3D image may be transferred here to analogous data structures and/or functions in the case of methods and apparatuses for the provision of trained functions. Analogous data structures may be identified here in particular by the use of the prefix "training". Furthermore, the trained functions used in methods and apparatuses for the provision of a transformation instruction for registering a 2D image with a 3D image may have been adjusted and/or provided in particular by methods and apparatuses for the provision of trained functions.

The disclosure relates in a first aspect to a computer-implemented method for the provision of a transformation instruction for registering a 2D image with a 3D image. Accordingly, it is provided that in act a) the 2D image and the 3D image are received. Furthermore, in act b), input data based on the 2D image including contour pixels and the 3D image including contour voxels is generated. The contour pixels are dependent on contour features of the 2D image. Furthermore, the contour voxels are dependent on the contour features of the 3D image. In addition, the contour voxels have a substantially perpendicular contour surface normal in respect of a specified projection direction. In act c), a trained function is applied to the input data for the identification of contour pixels of the 2D image and contour voxels of the 3D image, which correspond with each other. At least one parameter of the trained function is adjusted here based on a comparison of training contour pixels with comparison contour pixels and a comparison of training contour voxels corresponding thereto with comparison contour voxels. In a further act d), the transformation instruction is determined based on the identified contour pixels of the 2D image and the contour voxels of the 3D image corresponding thereto for registering the 2D image with the 3D image. Furthermore, the transformation instruction is provided in act f).

The 3D image may include three-dimensional medical image data of an examination region of an examination object. Advantageously, the 3D image may depict the examination region of the examination object, in particular, preoperatively. The 3D image may include a plurality of 2D slice images, moreover. In addition, the 3D image may have a 3D tissue parameter map. Furthermore, a pre-determined tissue region may be segmented and/or contrasted in the 3D image.

The examination object may include an animal patient and/or a human patient. Furthermore, the examination region of the examination object may include an anatomical and/or spatial region of the examination object, which has a pre-determined tissue region and/or a spatial region of a planned intervention.

The 3D image of the examination region of the examination object may be recorded and/or provided, in particular, by a medical imaging device, in particular preoperatively. The medical imaging device for recording the 3D image may be designed as a medical X-ray device, (e.g., as a C-arm X-ray device and/or Dyna-CT), and/or magnetic resonance system (MRT) and/or computed tomography system (CT) and/or ultrasound device.

Furthermore, the 3D image may advantageously include metadata. The metadata may include information on recording parameters and/or operating parameters of the medical imaging device for recording the 3D image.

Receiving the 3D image may include acquiring and/or reading-out from a computer-readable data memory and/or receiving from a data memory unit, for example, a database.

Furthermore, the 3D image may be provided by a processing unit of the medical imaging device for recording the 3D image.

The 2D image may include two-dimensional medical image data of the examination region of the examination object. Advantageously, the 2D image may depict the examination region of the examination object, in particular, intraoperatively. Advantageously, the 2D image may include a projection image of the examination region of the examination object depicted in the 3D image along a projection direction. Advantageously, the 2D image may depict at least one section of the examination region of the examination object depicted in the 3D image therefore. The 2D image may be designed, for example, as a projection X-ray image, in particular fluoroscopy image. In addition, the 2D image may have a tissue parameter map. Furthermore, a pre-determined tissue region and/or a medical instrument may be segmented and/or contrasted in the 2D image.

The 2D image of the examination region of the examination object may be recorded and/or provided, in particular intraoperatively, in particular by a medical imaging device. The medical imaging device for recording the 2D image may be designed as a medical X-ray device, (e.g., as a C-arm X-ray device and/or Dyna-CT), and/or magnetic resonance system (MRT) and/or computed tomography system (CT) and/or ultrasound device. The 2D image may be recorded after the 3D image.

Furthermore, advantageously the 2D image may include metadata. The metadata may include information on recording parameters and/or operating parameters of the medical imaging device for recording the 2D image.

Receiving the 2D image may include acquiring and/or reading-out from a computer-readable data memory and/or receiving from a data storage unit, for example, a database. Furthermore, the 2D image may be provided by a processing unit of the medical imaging device for recording the 2D image.

In particular, the 2D image and the 3D image may be recorded and/or provided by the same medical imaging device.

Advantageously, the 3D image includes a plurality of voxels, in particular, image points. Each voxel may have one value respectively, in particular, an image value, (e.g., a gray scale value and/or a RGB color value and/or an intensity value).

Analogously, the 2D image may include a plurality of pixels, in particular, image points. Each pixel may have one value respectively, in particular, one image value, (e.g., a gray scale value and/or a RGB color value and/or an intensity value).

The contour features of the 3D image may advantageously be specified using 3D shape information and/or structure information of the examination region of the examination object depicted in the 3D image. For example, the contour features of the 3D image may be depicted as contrasted transitions and/or borders between different tissue regions and/or anatomy features. In particular, a contour feature of the 3D image may enclose a pre-determined tissue region. Furthermore, the contour features of the 3D image may be designed as isolines and/or isoareas. The isolines and/or isoareas may be determined, for example, by one image value and/or contrast value and/or value of a tissue parameter of the 3D image, respectively. Furthermore, the isolines and/or isoareas may in each case run along a specified spatial distance, in particular, constantly spaced apart from each other along a spatial direction. The isolines and/or isoareas may be designed, for example, as contours of the 3D image.

Furthermore, voxels of the 3D image may be selected and/or determined as a function of the contour features of the 3D image as contour voxels. For example, all voxels, which are located within a specified spatial distance and/or image value range of a contour feature of the 3D image, may be selected and/or determined as contour voxels.

Advantageously, the contour features of the 2D image may be specified using 2D shape information and/or structure information of the examination region of the examination object depicted in the 2D image. For example, the contour features of the 2D image may be designed as contrasted transitions and/or borders between different tissue regions and/or anatomy features. In particular, a contour feature of the 2D image may enclose a pre-determined tissue region. Furthermore, the contour features of the 2D image may be designed as isolines. The isolines may be determined by one image value and/or contrast value and/or value of a tissue parameter of the 2D image respectively. Furthermore, the isolines may in each case run along a specified spatial distance, in particular, constantly spaced apart from each other along a spatial direction.

Furthermore, pixels of the 2D image may be selected and/or determined as a function of the contour features of the 2D image as contour pixels. For example, all pixels, which are located within a specified spatial distance and/or image value range of a contour feature of the 2D image, may be selected and/or determined as contour pixels.

Furthermore, each of the contour voxels, as a function of the associated contour feature, may have a contour surface normal. The contour surface normal may include a normal, in particular, a normal vector, perpendicular to the contour feature, in particular, to the isoline and/or isoarea of the contour feature, at the spatial position of the respective contour voxel.

Furthermore, a projection direction may be specified for mapping the 3D image onto a 2D projection image, in particular, the 2D image. Advantageously, the projection direction may be specified, in particular, initially, as a function of at least one recording parameter and/or operating parameter of the 2D image.

Advantageously, the contour voxels are selected and/or determined as a function of the contour features of the 3D image in such a way that the respective contour surface normal of the contour voxels is substantially perpendicular, in particular, not parallel, in respect of the specified projection direction. The contour voxels, which have a substantially parallel contour surface normal in respect of the specified projection direction, may overlap one another in the case of a projection image of the 3D image along the specified projection direction. Contour voxels, which in the case of the projection image overlap one another along the specified projection direction are not suitable for registering owing to the lack of differentiability, however. Due to the fact that only the contour voxels, which have a contour surface normal substantially perpendicular in respect of the specified projection direction, are selected and/or determined for the input data, almost overlap-free projection image of the associated contour feature along the specified projection direction may be provided. The selected contour voxels are in this case also differentiable according to the projection image along the specified projection direction therefore.

Advantageously, the input data generated in act b) includes the contour pixels of the 2D image and the contour voxels of the 3D image, which are, in particular selected and/or determined, as a function of the respective contour features.

Contour pixels of the 2D image and contour voxels of the 3D image, which correspond with each other, may be identified by application of the trained function to the input data generated in act b).

Advantageously, the trained function may be trained by a method of machine learning. In particular, the trained function may be a neural network, (e.g., a convolutional neural network (CNN) or a network including a convolutional layer).

A trained function maps input data onto output data. Here, the output data may, in particular, still depend on one or more parameter(s) of the trained function. The one or more parameter(s) of the trained function may be determined and/or adjusted by training. Determining and/or adjusting the one or more parameter(s) of the trained function may be based, in particular, on a pair of training input data and associated training output data, with the trained function being applied to the training input data to generate training image data. In particular, determining and/or adjusting may be based on comparison of the training image data and the training output data. A trainable function, (e.g., a function with one or more parameters which have not yet been adjusted), may also be called a trained function.

Other terms for trained function are trained mapping instruction, mapping instruction with trained parameters, function with trained parameters, algorithm based on artificial intelligence, machine learning algorithm. An example of a trained function is an artificial neural network, wherein the edge weights of the artificial neural network match the parameters of the trained function. Instead of the term "neuronal network", the term "neural network" may also be used. In particular, a trained function may also be a deep artificial neural network (deep neural network). A further example of a trained function is a "Support Vector Machine". In particular, other algorithms of machine learning may still be used as a trained function as well.

The trained function may be trained by a back propagation. The training image data may be determined by application of the trained function to training input data. In accordance with this, a difference between the training image data and the training output data may be determined by application of an error function to the training image data and the training output data. Furthermore, at least one parameter, (e.g., a weighting), of the trained function, (e.g., of the neural network), may be adjusted iteratively based on a gradient of the error function in respect of the at least one parameter of the trained function. The difference between the training image data and the training output data during training of the trained function may be advantageously minimized hereby.

Advantageously, the trained function, in particular the neural network, has an input slice and an output slice. The input slice may be designed for receiving input data. Furthermore, the output slice may be designed for providing mapping data. The input slice and/or the output slice may in each case include a plurality of channels, in particular neurons.

At least one parameter of the trained function may be adjusted to a comparison of training contour pixels with comparison contour pixels and a comparison of training contour voxels corresponding thereto with comparison contour voxels. Advantageously, the comparison contour voxels and the comparison contour pixels corresponding thereto may be identified as a function of the respective contour features, which have been identified in a 2D training image and a 3D training image. Furthermore, the training contour pixels and the training contour voxels may have been identified by application of the trained function to input data, which is based on the 2D training image and the 3D training image. Advantageously, the training contour voxels and the training contour pixels corresponding thereto may be identified as part of a proposed computer implemented method for the provision of a trained function, which will be described below.

Advantageously, the contour pixels and contour voxels identified in act c), which correspond with each other, may in each case be dependent on the same contour feature of the respective image. In particular, a contour pixel may in each case correspond with a contour voxel, wherein the contour pixel corresponds to a projection image of the contour voxel along the specified projection direction.

In act d), based on the identified contour pixels of the 2D image and the contour voxels of the 3D image corresponding thereto, a transformation instruction may be determined for registering the 2D image with the 3D image. The transformation instruction may include, in particular rigid and/or non-rigid, transformation of the 3D image. Advantageously, the 3D image may be transformed using the transformation instruction in such a way that the transformed 3D image, in the case of a projection image along the specified projection direction is mapped onto the 2D image. Advantageously, the transformation instruction may include a translation instruction and/or rotation instruction and/or interpolation instruction relating to the 3D image, in particular to the voxels of the 3D image.

Furthermore, the transformation instruction may include a transformation of the 2D image, in particular a rigid and/or non-rigid one. The 2D image may be transformed using the transformation instruction in such a way that the transformed 2D image is mapped onto a projection image of the 3D image along the specified projection direction.

Furthermore, the provision of the transformation instruction in act f) may include, in particular, storage on a computer-readable storage medium and/or display on a display unit and/or transfer to a processing unit.

In a further advantageous embodiment of the proposed computer-implemented method for the provision of a transformation instruction, the 2D image may include a projection image of an examination region of an examination object depicted in the 3D image, wherein the projection direction is specified in act b) as a function of the projection image. The 2D image of the examination region of the examination object may be recorded by a medical imaging device, in particular a C-arm X-ray device. Advantageously, the specified projection direction may be specified in respect of a coordinate system of the medical imaging device for recording the 2D image and/or a coordinate system of the examination object and/or a patient support apparatus. The projection direction may be specified particularly quickly and intuitively in act b) hereby.

Furthermore, a plurality of 2D images of the examination region of the examination object recorded in chronological order may be received. Here, the proposed computer-implemented method for the provision of the transformation instruction may be performed for one of the plurality of 2D images successively in each case. In particular, if the plurality of 2D images are recorded with different projection directions, the projection direction may in each case be specified in act b) using a recording parameter and/or operating parameter of the 2D image. Particularly flexible application of the proposed method may be enabled hereby.

In a further advantageous embodiment of the proposed computer-implemented method for the provision of a transformation instruction, the proposed method may also include act e), wherein the specified projection direction is adjusted as a function of the transformation instruction. Furthermore, acts b) to e) of the proposed method may be repeated until the occurrence of a termination condition. In particular, if the projection direction is specified in act b) in respect of a coordinate system of the 3D image, the specified projection direction may be adjusted using the transformation instruction determined in act d). As a result, a particularly computing-efficient adjustment of the projection image of the 3D image may be enabled along the specified projection direction for registering with the 2D image. Advantageously, acts b) to e) may be repeated, in particular iteratively, until the occurrence of a termination condition. The accuracy of the transformation instruction in respect of registering the 2D image with the 3D image may be advantageously iteratively improved hereby. On the occurrence of the termination condition, the (e.g., last) determined transformation instruction may be provided in act f).

In the process, the termination condition may include a maximum number of repetitions and/or a threshold value in respect of a cost value of registering the 2D image with the 3D image. Furthermore, the termination condition may advantageously occur on reaching and/or exceeding the maximum number of repetitions of acts b) to e) and/or on reaching and/or exceeding the threshold value in respect of the cost value. By specifying a threshold value in respect of the cost value as a termination condition, advantageously, a quality, (e.g., a minimum quality), may be specified for registering the 2D image with the 3D image. Furthermore, the runtime of the proposed computer-implemented method for the provision of the transformation instruction may be limited by specifying a maximum number of repetitions as the termination condition. This may be advantageous in particular in a clinical environment.

In a further advantageous embodiment of the proposed computer-implemented method for the provision of a transformation instruction, act b) may include generation of a gradient image from the 3D image by applying a projection mapping. Furthermore, the input data may still be based on the gradient image. The gradient image may be two-dimensional in particular. Furthermore, the gradient image may advantageously include a plurality of pixels, in particular gradient pixels. For generation of the gradient image the projection image may include determination of the gradient values of the values of the voxels of the 3D image in respect of adjacent voxels. Furthermore, alternatively or in addition, the projection image may include determination of the gradient values of the voxels of the 3D image along two spatial directions. Advantageously, the projection image for the generation of the gradient image from the 3D image may take place along the specified projection direction. Advantageously, the contour features of the 3D image may be particularly reliably identified and/or determined hereby in the gradient image. The gradient image, (e.g., the contour features contained therein), generated in act b) from the 3D image, may be conducive to selection and/or determination of the contour voxels of the 3D image. Furthermore, by considering the gradient image in act b), the contour voxels of the 3D image, whose contour surface normal is substantially perpendicular in respect of the specified projection direction, may be selected and/or determined in a particularly computing-efficient and intuitive manner.

In a further advantageous embodiment of the proposed computer-implemented method for the provision of a transformation instruction, act b) may also include generation of a second gradient image from the 2D image. In addition, the input data may also be based on the second gradient image. The second gradient image may be two-dimensional. Furthermore, the second gradient image may advantageously include a plurality of pixels, in particular gradient pixels. Generation of the second gradient image may advantageously include determination of the gradient values of the values of the pixels of the 2D image in respect of adjacent pixels. Furthermore, generation of the second gradient image may alternatively or in addition include determination of the gradient values of the pixels of the 2D image along two spatial directions. Advantageously, the contour features of the 2D image in the second gradient image may be identified and/or determined particularly reliably hereby. The second gradient image, in particular the contour features contained therein, generated in act b) from the 2D image may be conducive to selection and/or determining of the contour pixels of the 2D image.

In a further advantageous embodiment of the proposed computer-implemented method for the provision of a transformation instruction, act a) may also include receiving a movement parameter, in particular, of the examination object. Advantageously, the contour features of the 2D image may be adjusted in act b) using the movement parameter. Here, the movement parameter may include information on an at least progressive movement and/or change in the examination region of the examination object, in particular with respect to the 3D image. Furthermore, the movement parameter may advantageously include a physiological parameter, (e.g., a breathing signal and/or a pulse signal), of the examination object at the instant of recording of the 2D image. Receiving the movement parameter may include acquiring and/or reading out from a computer-readable data memory and/or receiving from a data memory unit, (e.g., a database). Furthermore, the movement parameter may be provided by a movement detection unit designed to record a movement and/or change in the examination region of the examination object.

Furthermore, the contour features of the 2D image may be adjusted, (e.g., non-rigidly and/or rigidly transformed), in act b) using the movement parameter. A robustness of the proposed method, (e.g., with respect to a movement of the examination object after recording the 3D image), may be improved hereby.

The disclosure relates in a second aspect to a computer-implemented method for registering a 2D image with a 3D image. Here, in act r.a), a transformation instruction, the 2D image, and the 3D image are received. Furthermore, the transformation instruction is advantageously provided by a proposed computer-implemented method for the provision of a transformation instruction for registering a 2D image with a 3D image. Furthermore, in act r.b), the 2D image is registered with the 3D image based on the transformation instruction. In act r.c), the registered 3D image is provided.

Receiving the 2D image, the 3D image, and the transformation instruction in act r.a) may include acquiring and/or reading-out from a computer-readable data memory and/or receiving from a data memory unit, for example, a database. Furthermore, the 2D image and/or the 3D image may be provided by a processing unit of the medical imaging device.

In act r.b), registering the 2D image with the 3D image may include, (e.g., non-rigid and/or rigid), transformation of the 3D image according to the transformation instruction. Advantageously, the transformation instruction may include a translation instruction and/or rotation instruction and/or an interpolation instruction relating to the 3D image, in particular, to the voxels of the 3D image. Registering the 2D image with the 3D image may take place in respect of the projection direction in relation to the projection image during recording of the 2D image.

Furthermore, the provision of the registered 3D image in act r.c) may include storage on a computer-readable storage medium and/or display on a display unit and/or transfer to a processing unit.

Advantageously, the registered 3D image may be provided intraoperatively in order to support medical personnel.

The advantages of the proposed computer-implemented method for registering a 2D image with a 3D image substantially correspond to the advantages of the proposed computer-implemented method for the provision of a transformation instruction for registering a 2D image with a 3D image. Features, advantages, or alternative embodiments mentioned in this connection may likewise be transferred to the other claimed subject matters and vice versa.

The disclosure relates in a third aspect to a computer-implemented method for the provision of a trained function. In act r.a), a 2D training image and a 3D training image are received. Furthermore, in act t.b), comparison contour voxels of the 3D training image and comparison contour pixels of the 2D training image are identified, which correspond with each other. For this, contour features of the 3D training image are identified in a first act i). Furthermore, in act ii), contour features of the 2D training image are identified. In act iii), the contour features of the 2D training image and the contour features of the 3D training image are then selected, which correspond with each other. In act iv), the comparison contour pixels of the 2D training image and the comparison contour voxels of the 3D training image are selected as a function of the contour features selected in act iii).

Furthermore, input data is generated based on the 2D training image including training contour pixels and the 3D training image including training contour voxels in act t.c). The training contour pixels are dependent on training contour features of the 2D training image. Furthermore, the training contour voxels are dependent on the training contour features of the 3D training image, which training contour voxels of the 3D training image, in respect of the specified projection direction, have a substantially perpendicular contour surface normal. In act t.d), the trained function is applied to the input data for the identification of training contour pixels of the 2D training image and training contour voxels of the 3D training image, which correspond with each other. Furthermore, in act t.e), at least one parameter of the trained function is adjusted based on a comparison of the training contour pixels with the comparison contour pixels and a comparison of training contour voxels corresponding thereto with the comparison contour voxels. The trained function is provided in act t.f).

The 3D training image may have all properties of the 3D image, which are described herein in relation to the computer-implemented method for the provision of a transformation instruction for registering a 2D image with a 3D image and vice versa. In particular, the 3D training image may be a 3D image. The 3D training image may include three-dimensional medical image data of an examination region of an examination object. Advantageously, the 3D training image may depict the examination region of the examination object, in particular preoperatively. The 3D training image may also include a plurality of 2D slice images. In addition, the 3D training image may have a 3D tissue parameter map. Furthermore, a pre-determined tissue region may be segmented and/or contrasted in the 3D training image.

The 3D training image of the examination region of the examination object may be recorded and/or provided, in particular preoperatively, in particular by a medical imaging device. The medical imaging device for recording the 3D training image may be designed as a medical X-ray device, (e.g., as a C-arm X-ray device and/or Dyna-CT, and/or magnetic resonance system (MRT) and/or computed tomography system (CT) and/or ultrasound device).

Furthermore, the 3D training image may advantageously include metadata. The metadata may include information on recording parameters and/or operating parameters of the medical imaging device for recording the 3D training image.

Receiving the 3D training image may include acquiring and/or reading-out from a computer-readable data memory and/or receiving from a data memory unit, (e.g., a database). Furthermore, the 3D training image may be provided by a processing unit of the medical imaging device for recording the 3D training image.

The 2D training image may have all properties of the 2D image, which were described in relation to the computer-implemented method for the provision of a transformation instruction for registering a 2D image with a 3D image and vice versa. In particular, the 2D training image may be a 2D image. The 2D training image may include two-dimensional medical image data of an examination region of an examination object. Advantageously, the 2D training image may depict the examination region of the examination object, in particular intraoperatively. Advantageously, the 2D training image may include a projection image of the examination region of the examination object depicted in the 3D training image along one projection direction. Advantageously, the 2D training image may therefore depict at least one detail of the examination region of the examination object depicted in the 3D training image. The 2D training image may be depicted as a projection X-ray image, in particular, fluoroscopy image. In addition, the 2D training image may have a tissue parameter map. Furthermore, a pre-determined tissue region and/or a medical instrument may be segmented and/or contrasted in the 2D training image.

The 2D training image of the examination region of the examination object may be recorded and/or provided, in particular intraoperatively, in particular by a medical imaging device. The medical imaging device for recording the 2D training image may be designed as a medical X-ray device, (e.g., a C-arm X-ray device and/or Dyna-CT, and/or magnetic resonance system (MRT) and/or computed tomography system (CT) and/or ultrasound device). The 2D training image may be recorded after the 3D training image.

Furthermore, the 2D training image may advantageously include metadata. The metadata may include information on recording parameters and/or operating parameters of the medical imaging device for recording the 2D training image.

Receiving the 2D training image may include acquiring and/or reading-out from a computer-readable data memory and/or receiving from a data memory unit, (e.g., a database). Furthermore, the 2D training image may be provided by a processing unit of the medical imaging device for recording the 2D image.

In particular, the 2D training image and the 3D training image may be recorded and/or provided by the same medical imaging device. Furthermore, the 2D training image and/or the 3D training image may be simulated.

Advantageously, the 3D training image includes a plurality of voxels, in particular image points. Each voxel may each have one value respectively, in particular one image value, (e.g., a gray scale value and/or a RGB color value and/or an intensity value).

Analogously, the 2D training image may include a plurality of pixels, in particular image points. Each pixel may have one value respectively, in particular one image value, (e.g., a gray scale value and/or an RGB color value and/or an intensity value).

The comparison contour voxels of the 3D training image and comparison contour pixels corresponding thereto of the 2D training image may be identified in a computer-implemented manner according to acts i) to iv). Furthermore, acts i) to iv) may be performed semi-automatically, (e.g., by annotation of the 2D training image and/or of the 3D training image in the framework of supervised learning). In particular, an annotated 2D training image and/or an annotated 3D training image may be received in act t.a), wherein comparison contour pixels and/or comparison contour voxels that correspond with each other may be annotated in the respective annotated training image.

Advantageously, the contour features of the 3D training image may be identified in act i). For example, an algorithm for pattern recognition and/or edge recognition may be applied to the 3D training image for this. The identification of the contour features of the 3D training image may be based on the image values of the voxels of the 3D training image. The contour features of the 2D training image may be identified as in act ii).

Furthermore, the contour features of the 2D training image and the contour features of the 3D training image, which correspond with each other, may be selected in act iii). For example, an algorithm for pattern recognition and/or edge recognition, starting from the contour features of the 2D training image, may select the contour features of the 3D training image corresponding thereto, (e.g., after a projection image of the 3D training image along the specified projection direction). Furthermore, an algorithm for pattern recognition and/or edge recognition, starting from contour features of a projection image of the 3D training image along the specified projection direction, may select the contour features of the 2D training image corresponding thereto.

In accordance with this, the comparison contour pixels of the 2D training image and the comparison contour voxels of the 3D training image may be selected in act iv) as a function of the selected contour features, which correspond with each other. Because the comparison contour pixels and the comparison contour voxels are already dependent on a contour feature of the respective training image, advantageously these may be selected, corresponding to the contour features selected in act iii). Advantageously, the comparison contour pixels and comparison contour voxels selected in act iv), which correspond with each other, may each be dependent on the same contour feature of the respective training image.

Advantageously, the training contour features of the 3D training image may be specified using 3D shape information and/or structure information of the examination region of the examination object depicted in the 3D training image. For example, the training contour features of the 3D training image may be designed as contrasted transitions and/or borders between different tissue regions and/or anatomy features. In particular, a training contour feature of the 3D training image may enclose pre-determined tissue region. Furthermore, the training contour features of the 3D training image may be designed as isolines and/or isoareas. The isolines and/or isoareas may be determined by one image value and/or contrast value and/or value of a tissue parameter of the 3D image respectively. Furthermore, the isolines and/or isoareas may in each case run along a specified spatial distance, in particular along a spatial direction so as to be constantly spaced apart from each other. The isolines and/or isoareas may be designed as contours of the 3D image.

Furthermore, as a function of the training contour features of the 3D training image, voxels of the 3D training image may be selected and/or determined as training contour voxels. For example, all voxels, which are located within a specified spatial distance and/or image value range of a training contour feature of the 3D training image, may be selected and/or determined as training contour voxels.

Advantageously, the training contour features of the 2D training image may be specified using 2D shape information and/or structure information of the examination region of the examination object depicted in the 2D training image. For example, the training contour features of the 2D training image may be designed as contrasted transitions and/or borders between different tissue regions and/or anatomy features. In particular, a training contour feature of the 2D training image may enclose a pre-determined tissue region. Furthermore, the training contour features of the 2D training image may be designed as isolines. The isolines may be determined by one image value and/or contrast value and/or value of a tissue parameter of the 2D training image respectively. Furthermore, the isolines may each run along a specified spatial distance, in particular along a spatial direction so as to be constantly spaced apart from each other.

Furthermore, as a function of the training contour features, pixels of the 2D training image may be selected and/or determined as training contour pixels. For example, all pixels, which are located within a specified spatial distance and/or image value range of a training contour feature of the 2D training image, may be selected and/or determined as training contour pixels.

Furthermore, as a function of the associated training contour feature, each of the training contour voxels may have a contour surface normal. The contour surface normal may include a normal, (e.g., a normal vector), perpendicular to the training contour feature of the 3D training image, (e.g., to the isoline and/or isoarea of the training contour feature), at the spatial position of the respective training contour voxels.

Advantageously, the training contour voxels are selected and/or determined as a function of the training contour features of the 3D training image in such a way that the respective contour surface normal of the training contour voxels is substantially perpendicular in respect of the specified projection direction.

Advantageously, the input data generated in act t.c) includes the training contour pixels of the 2D training image and the training contour voxels of the 3D training image, which are, in particular, selected and/or determined as a function of the respective training contour features.

By applying the trained function to the input data generated in act t.c), training contour pixels of the 2D training image and training contour voxels of the 3D training image, which correspond with each other, may be identified in act t.d).

In act t.e), at least one parameter of the trained function may be adjusted based on a comparison of the training contour pixels, (e.g., a spatial position of the training contour pixels in respect of the 2D training image), with the comparison contour pixels, (e.g., a spatial position of the comparison contour pixels in respect of the 2D training image), and a comparison of training contour voxels corresponding thereto, (e.g., a spatial position of the training contour voxels in respect of the 3D training image), with the comparison contour voxels, (e.g., a spatial position of the comparison contour voxels in respect of the 3D training image).

Furthermore, the provision of the trained function in act t.f) may include storage on a computer-readable storage medium and/or display on a display unit and/or transfer to a processing unit.

Advantageously, a trained function may be provided with the proposed method, which may be used in the computer-implemented method for the provision of a transformation instruction for registering a 2D image with a 3D image.

In a further advantageous embodiment of the proposed computer-implemented method for the provision of a trained function, the 2D training image may include a projection image of an examination region of an examination object depicted in the 3D training image, wherein the projection direction is specified in act t.c) as a function of the projection image. The 2D training image of the examination region of the examination object may be recorded by a medical imaging device, (e.g., a C-arm X-ray device). Advantageously, the specified projection direction in respect of a coordinate system of the medical imaging device may be specified for recording the 2D training image and/or a coordinate system of the examination object and/or a patient support apparatus. The projection direction may be specified particularly quickly and intuitively in act t.c) hereby.

In a further advantageous embodiment of the proposed computer-implemented method for the provision of a trained function, act t.c) may also include generation of a training gradient image from the 3D training image by applying a projection mapping. Furthermore, the input data of the trained function may also be based on the training gradient image. The training gradient image may be two-dimensional. Furthermore, the training gradient image may advantageously include a plurality of pixels, (e.g., training gradient pixels). The projection image, for generation of the training gradient image, may include determination of the gradient values of the values of the voxels of the 3D training image in respect of adjacent voxels. Furthermore, the projection image may alternatively or in addition include determination of the gradient values of the voxels of the 3D training image along two spatial directions. Advantageously, the projection image for the generation of the training gradient image from the 3D training image may take place along the specified projection direction. Advantageously, the training contour features of the 3D training image may be identified and/or determined particularly reliably in the training gradient image. The training gradient image generated from the 3D training image in act t.c), in particular the training contour features contained therein, may be conducive to selection and/or determination of the training contour voxels of the 3D training image. Furthermore, by considering the training gradient image in act t.c), the training contour voxels of the 3D training image, whose contour surface normal is substantially perpendicular in respect of the specified projection direction, may be selected and/or determined in a particularly computing-efficient and intuitive manner.

In a further advantageous embodiment of the proposed computer-implemented method for the provision of a trained function, act t.c) may also include generation of a second training gradient image from the 2D training image. In addition, the input data may also be based on the second training gradient image. The second training gradient image may be two-dimensional. Furthermore, the second training gradient image may advantageously include a plurality of pixels, in particular training gradient pixels. Advantageously, generation of the second training gradient image may include determination of the gradient values of the values of the pixels of the 2D training image in respect of adjacent pixels. Furthermore, generation of the second training gradient image may alternatively or in addition include determination of the gradient values of the pixels of the 2D training image along two spatial directions. Advantageously, the training contour features of the 2D training image may be identified and/or determined particularly reliably in the second training gradient image hereby. The second training gradient image generated in act b) from the 2D training image, in particular the training contour features contained therein, may be conducive to selection and/or determination of the training contour pixels of the 2D training image.

In a further advantageous embodiment of the proposed computer-implemented method for the provision of a trained function, act t.a) may also include receiving a training movement parameter. The contour features of the 2D training image in act t.b) and the training contour features of the 2D training image in act t.c) may also be adjusted using the training movement parameter.

The training movement parameter may have all properties of the movement parameter, which were described in relation to the computer-implemented method for the provision of a transformation instruction for registering a 2D image with a 3D image and vice versa. In particular, the training movement parameter may be a movement parameter. The training movement parameter may include information on at least progressive movement and/or change in the examination region of the examination object, (e.g., with respect to the 3D training image). Furthermore, the training movement parameter may advantageously include a physiological parameter, (e.g., a breathing signal and/or a pulse signal), of the examination object at the instant of recording of the 2D training image. Receiving the training movement parameter may include acquiring and/or reading-out from a computer-readable data memory and/or receiving from a data memory unit, (e.g., a database). Furthermore, the training movement parameter may be provided by a movement detection unit designed to detect a movement and/or change in the examination region of the examination object.

Furthermore, the contour features of the 2D image may be adjusted, (e.g., non-rigidly and/or rigidly transformed), in act t.b) and the training contour features of the 2D training image in act t.c) using the training movement parameter. A robustness of the proposed method, (e.g., with respect to a movement of the examination object after recording of the 3D training image), may be improved hereby.

The disclosure relates in a fourth aspect to a processing unit for the provision of a transformation instruction for registering a 2D image with a 3D image. Advantageously, the proposed processing unit includes an arithmetic unit and an interface. The interface is designed for receiving the 2D image and the 3D image. Furthermore, the arithmetic unit is designed for generation of input data based on the 2D image including contour pixels and the 3D image including contour voxels. The contour pixels are dependent on contour features of the 2D image. Furthermore, the contour voxels are dependent on contour features of the 3D image, which contour voxels of the 3D image have a substantially perpendicular contour surface normal in respect of a specified projection direction. Furthermore, the arithmetic unit is designed for application of a trained function to the input data for identification of contour pixels of the 2D image and contour voxels of the 3D image, which correspond with each other. At least one parameter of the trained function is adjusted based on a comparison of training contour pixels with comparison contour pixels and a comparison of training contour voxels corresponding thereto with comparison contour voxels. Furthermore, the arithmetic unit is designed for determining a transformation instruction based on the identified contour pixels of the 2D image and the contour voxels corresponding thereto of the 3D image for registering the 2D image with the 3D image. In addition, the interface is designed for the provision of the transformation instruction.

A processing unit of this kind may be designed to perform the above-described methods for the provision of a transformation instruction for registering a 2D image with a 3D image and their aspects. The processing unit is designed to carry out this method and its aspects in that the interface and the arithmetic unit are designed to carry out the corresponding method acts.

The disclosure relates in a fifth aspect to a medical imaging device including a proposed processing unit for the provision of a transformation instruction for registering a 2D image with a 3D image. The medical imaging device is advantageously designed for carrying out an embodiment of the proposed computer-implemented method for the provision of a transformation instruction for registering a 2D image with a 3D image and/or of the proposed method for registering a 2D image with a 3D image. Furthermore, the medical imaging device may be designed for recording and/or receiving the 2D image and/or the 3D image of an examination object.

The medical imaging device may include a display unit, (e.g., a display and/or a monitor), which is designed to display information and/or graphic displays of information of the medical imaging device and/or the processing unit and/or further components. In particular, the display unit may be designed to display a graphic display of the 2D image and/or the 3D image and/or the gradient image and/or the second gradient image and/or the transformation instruction.

The advantages of the proposed medical imaging device substantially match the advantages of the proposed computer-implemented method for the provision of a transformation instruction for registering a 2D image with a 3D image. Features, advantages, or alternative embodiments mentioned in this connection may likewise be transferred to the other claimed subject matters, and vice versa.

The disclosure relates in a sixth aspect to a training unit for the provision of a trained function. The training unit advantageously includes a training interface and a training arithmetic unit. Furthermore, the training interface is designed for receiving a 2D training image and a 3D training image. Furthermore, the training arithmetic unit is designed for the identification of comparison contour voxels of the 3D training image and comparison contour pixels of the 2D training image, which correspond with each other. Contour features of the 3D image are identified in a first act t.i). In addition, contour features of the 2D training image are identified in act t.ii). Furthermore, the contour features of the 2D training image and the contour features of the 3D training image, which correspond with each other, are selected in act t.iii). The comparison contour pixels of the 2D training image and the comparison contour voxels of the 3D training image are selected in act t.iv) as a function of the contour features selected in act t.iii). Advantageously, the training arithmetic unit is designed to carry out acts t.i) to t.iv).

Furthermore, the training arithmetic unit may be designed for generation of input data based on the 2D training image including training contour pixels and the 3D training image including training contour voxels. The training contour pixels may be dependent on training contour features of the 2D training image. Furthermore, the training contour pixels may be dependent on training contour features of the 3D training image, which training contour voxels of the 3D training image, in respect of the specified projection direction, have a substantially perpendicular contour surface normal. Furthermore, the training arithmetic unit may be designed for application of the trained function to the input data for the identification of training contour pixels of the 2D training image and training contour voxels of the 3D training image, which correspond with each other. In addition, the training arithmetic unit may be designed for adjusting at least one parameter of the trained function based on a comparison of the training contour pixels with the comparison contour pixels and a comparison of the training contour voxels corresponding thereto with the comparison contour voxels. Furthermore, the training interface may be designed for the provision of the trained function.

A training unit of this kind may be designed to carry out the above-described methods for the provision of a trained function and their aspects. The training unit is designed to carry out these methods and their aspects in that the training interface and the training arithmetic unit are designed to carry out the corresponding method acts.

The disclosure relates in a seventh aspect to a computer program product with a computer program, which may be loaded directly into a memory of a processing unit, with program segments in order to carry out all acts of the computer-implemented method for the provision of a transformation instruction for registering a 2D image with a 3D image or its aspects and/or the computer-implemented method for registering a 2D image with a 3D image when the program segments are run by the processing unit; and/or which may be loaded directly into a training memory of a training unit, with program segments in order to carry out all acts of the method for the provision of a trained function or one of its aspects when the program segments are run by the training unit.

The disclosure relates in an eighth aspect to a computer-readable storage medium on which program segments which may be read and run by a processing unit are stored in order to carry out all acts of the computer-implemented method for the provision of a transformation instruction for registering a 2D image with a 3D image or its aspects and/or the computer-implemented method for registering a 2D image with a 3D image when the program segments are run by the processing unit; and/or on which program segments which may be read and run by a training unit are stored in order to carry out all acts of the method for the provision of a trained function or one of its aspects when the program segments are run by the training unit.

The disclosure relates in a ninth aspect to a computer program or computer-readable storage medium, including a trained function provided by a method for the provision of a trained function or one of its aspects.

An implementation largely in terms of software has the advantage that even previously used processing units and/or training units may be easily retrofitted by way of a software update in order to operate as described herein. Apart from the computer program, a computer program product of this kind may optionally include additional components, such as documentation and/or additional components, as well as hardware components, such as hardware keys (e.g., dongles, etc.) for using the software.

BRIEF DESCRIPTION OF THE DRAWINGS

Exemplary embodiments are shown in the drawings and will be described in more detail below. Identical reference numerals are used in different figures for identical features. In the drawings.

DETAILED DESCRIPTION

Figure 1:
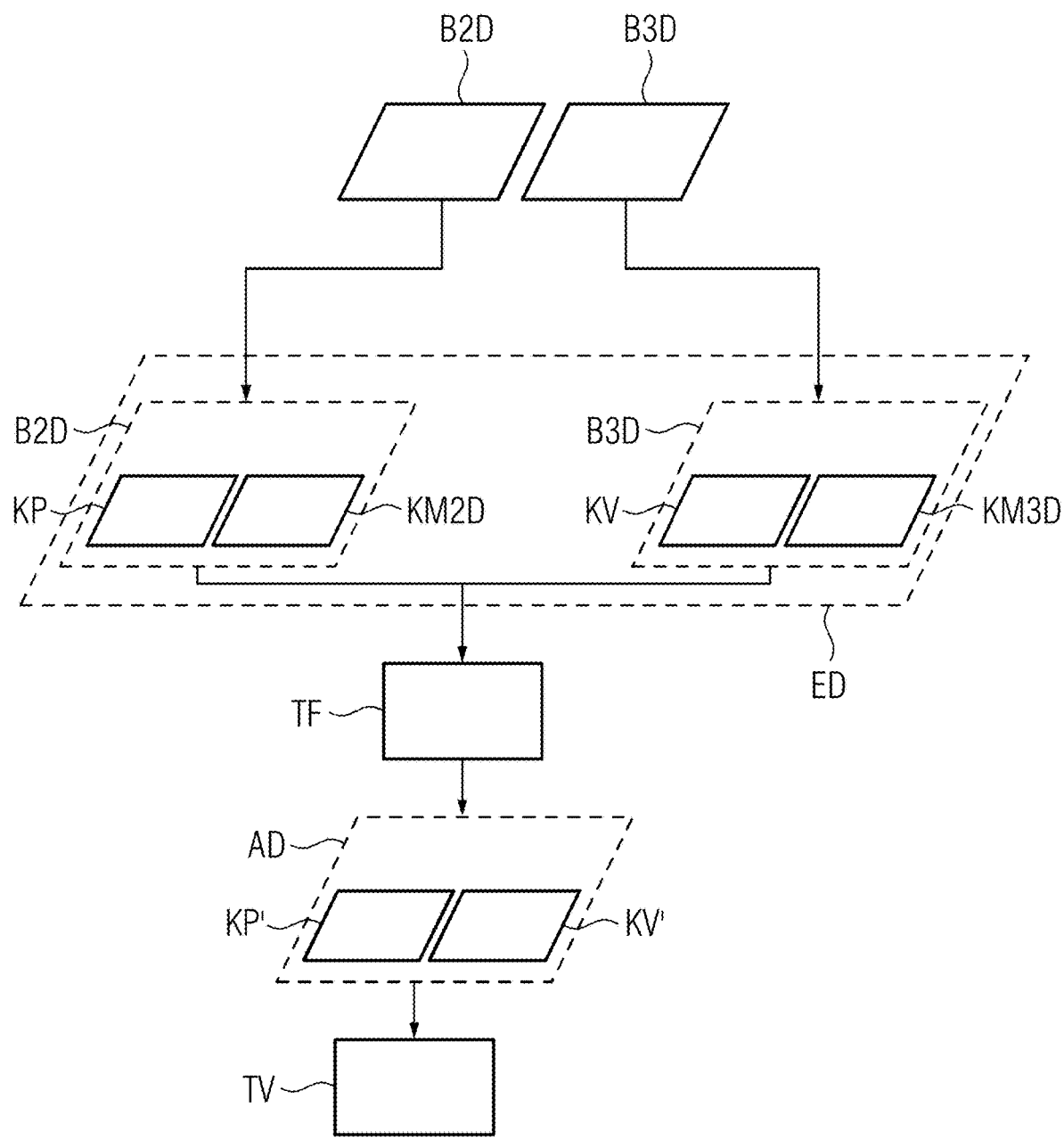
FIGS. 1 to 3 depict schematic representations of a data flow of different embodiments of a computer-implemented method for the provision of a transformation instruction for registering a 2D image with a 3D image.

FIG. 1 schematically depicts a data flow of a proposed computer-implemented method for the provision of a transformation instruction for registering a 2D image with a 3D image. A 2D image B2D and a 3D image B3D may be received in a first act a) here. Furthermore, input data ED may be generated in act b) based on the 2D image B2D including contour pixels KP and the 3D image B3D including contour voxels KV. The contour pixels KP are dependent on contour features KM2D of the 2D image B2D. Furthermore, the contour voxels KV are dependent on contour features KM3D of the 3D image B3D, which contour voxels KV of the 3D image KM3D have a substantially perpendicular contour surface normal in respect of a specified projection direction. In act c), a trained function TF may be applied to the input data ED for the identification of contour pixels KP' of the 2D image B2D and contour voxels KV' of the 3D image B3D, which correspond with each other. At least one parameter of the trained function TF may be adjusted to a comparison of training contour pixels with comparison contour pixels and a comparison of training contour voxels corresponding thereto with comparison contour voxels. The identified contour pixels KP' and contour voxels KV', which correspond with each other, may be regarded as imaging data AD of the trained function TF. In a further act d), the transformation instruction TV may be determined based on the identified contour pixels KP' of the 2D image B2D and the contour voxels KV', of the 3D image B3D corresponding thereto for registering the 2D image B2D with the 3D image B3D. The transformation instruction TV may be provided in act f).

Figure 2:
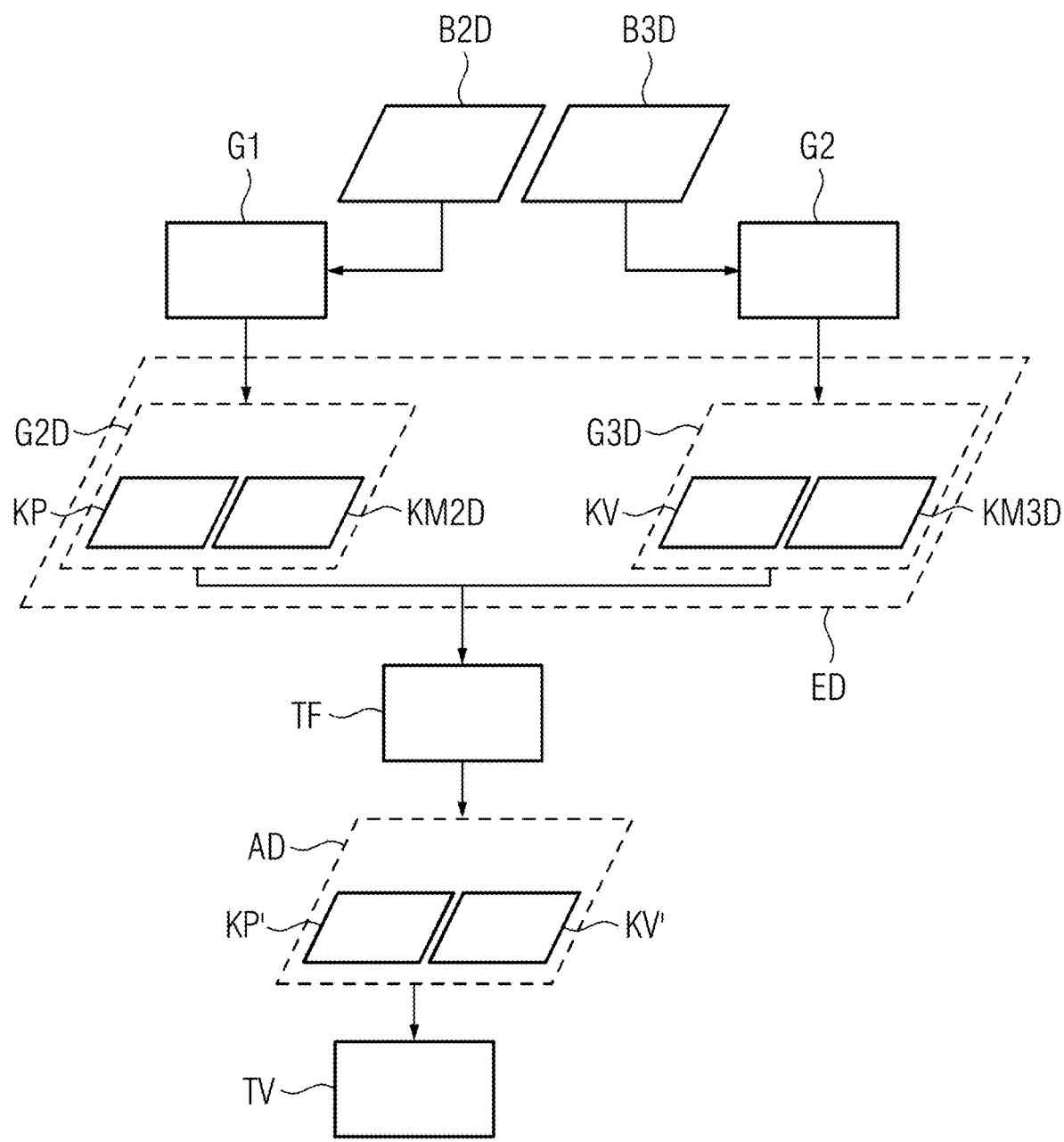

In the embodiment illustrated in FIG. 2 of the proposed computer-implemented method for the provision of a transformation instruction TV for registering a 2D image B2D with a 3D image B3D, a gradient image G3D may be generated from the 3D image B3D by applying a projection mapping G2. Furthermore, a second gradient image G2D may be generated from the 2D image B2D. Advantageously, generation of the second gradient image G2D may include determination G1 of the gradient values of the values of the pixels of the 2D image B2D in respect of adjacent pixels. Furthermore, generation of the second gradient image G2D may alternatively or in addition include determination G1 of the gradient values of the pixels of the 2D image B2D along two spatial directions. In addition, the input data ED may also be based on the gradient image G3D and/or the second gradient image G2D.

Figure 3:
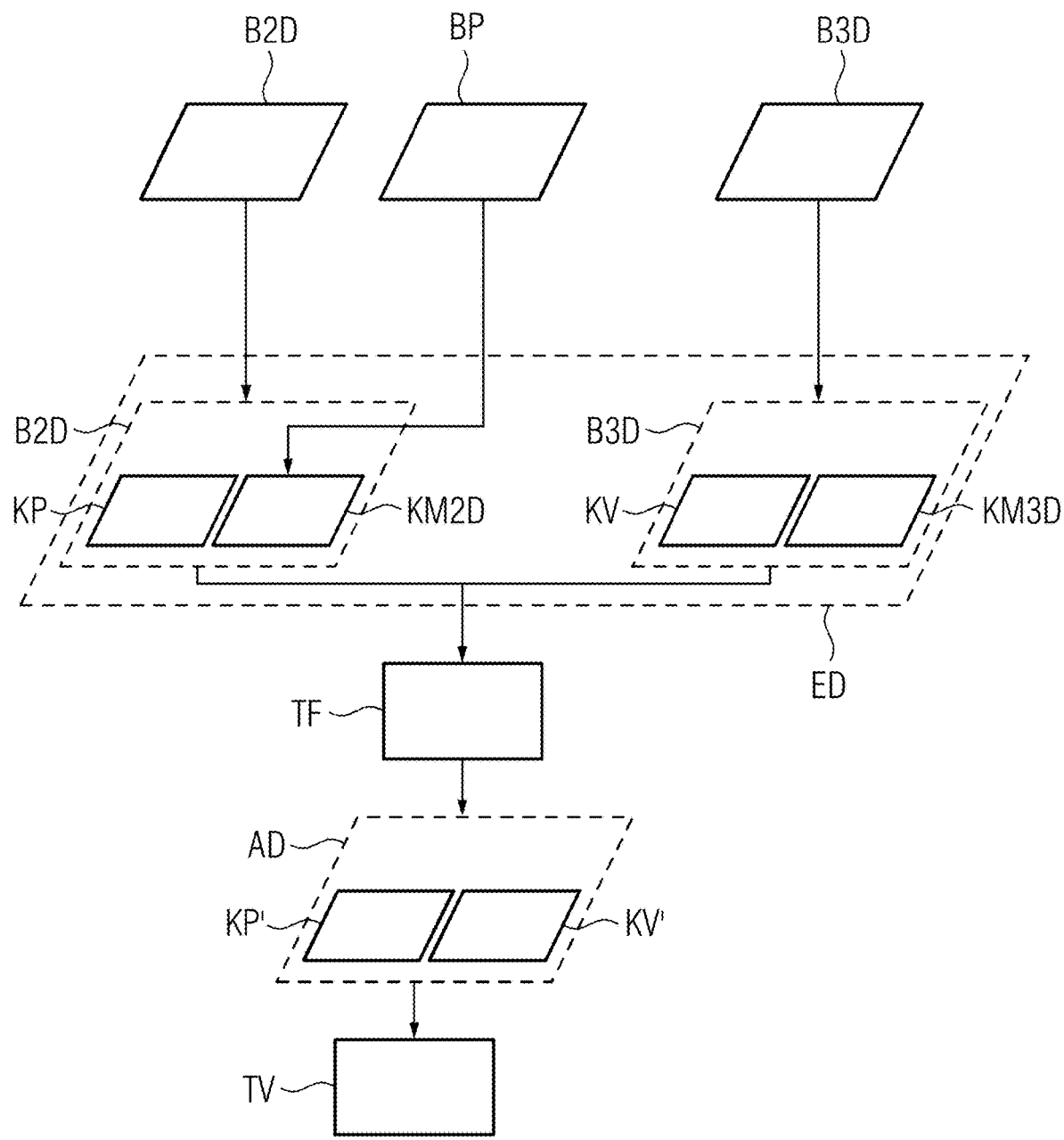

In the embodiment illustrated in FIG. 3 of the proposed computer-implemented method for the provision of a transformation instruction TV for registering a 2D image B2D with a 3D image B3D, act a) may also include receiving a movement parameter BP. The contour features KM2D of the 2D image B2D may be adjusted in act b) using the movement parameter BP.

Figure 4:
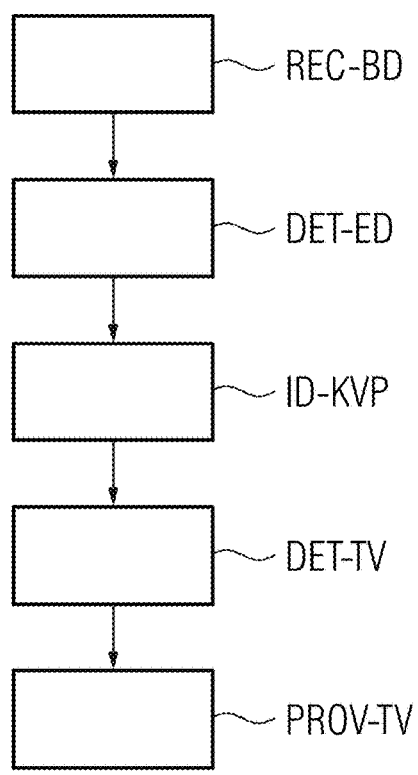
FIGS. 4 to 6 depict schematic flowcharts of different embodiments of a computer-implemented method for the provision of a transformation instruction for registering a 2D image with a 3D image.

FIG. 4 schematically illustrates a flowchart of a proposed computer-implemented method for the provision of a transformation instruction TV for registering a 2D image B2D with a 3D image B3D. The 2D image B2D and the 3D image B3D may be received REC-BD in a first act a). Furthermore, the input data ED may be generated DET-ED in a second act b) based on the 2D image B2D including contour pixels KP and the 3D image B3D including contour voxels KV. The trained function TF may be applied in a third act c) to the input data ED for the identification ID-KVP of contour pixels KP' of the 2D image B2D and contour voxels KV' of the 3D image B3D, which correspond with each other. Furthermore, the transformation instruction TV for registering the 2D image B2D with the 3D image B3D may be determined DET-TV in act d) based on the identified contour pixels KP' of the 2D image B2D and the contour voxels KV' corresponding thereto of the 3D image B3D. The transformation instruction TV may be provided PROV-TV in act f).

Furthermore, the 2D image B2D may include a projection image of an examination region of an examination object depicted in the 3D image B3D. The projection direction may be specified in act b) as a function of the projection image.

Figure 5:
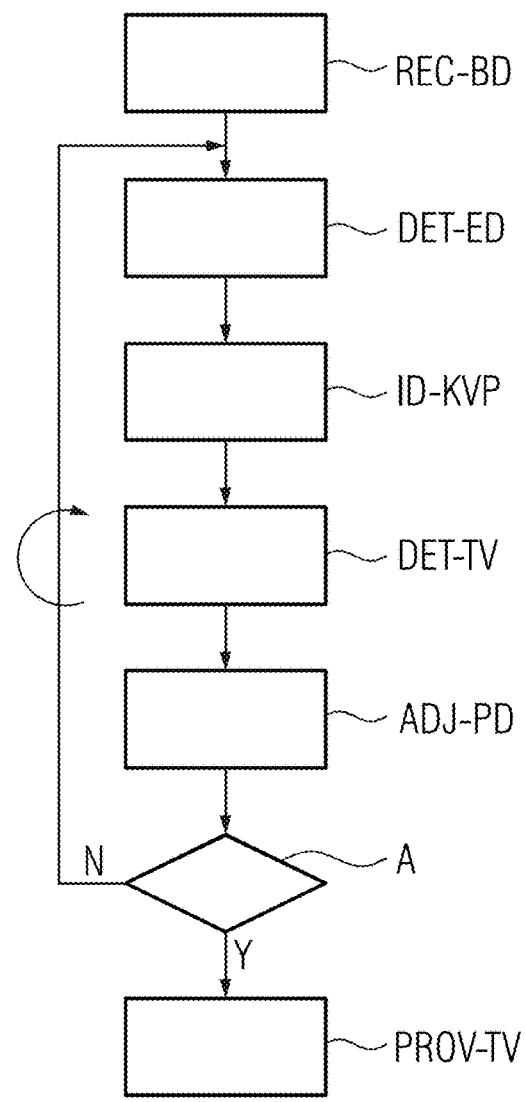

FIG. 5 depicts a further embodiment of the proposed computer-implemented method for the provision PROV-TV of a transformation instruction TV for registering a 2D image B2D with a 3D image B3D. The proposed method may also include act e), with the specified projection direction being adjusted ADJ-PD as a function of the transformation instruction TV. Furthermore, acts b) to e) may be repeated until the occurrence of a termination condition A. In particular, the transformation instruction TV may be provided on the occurrence of the termination condition A.

Figure 6:
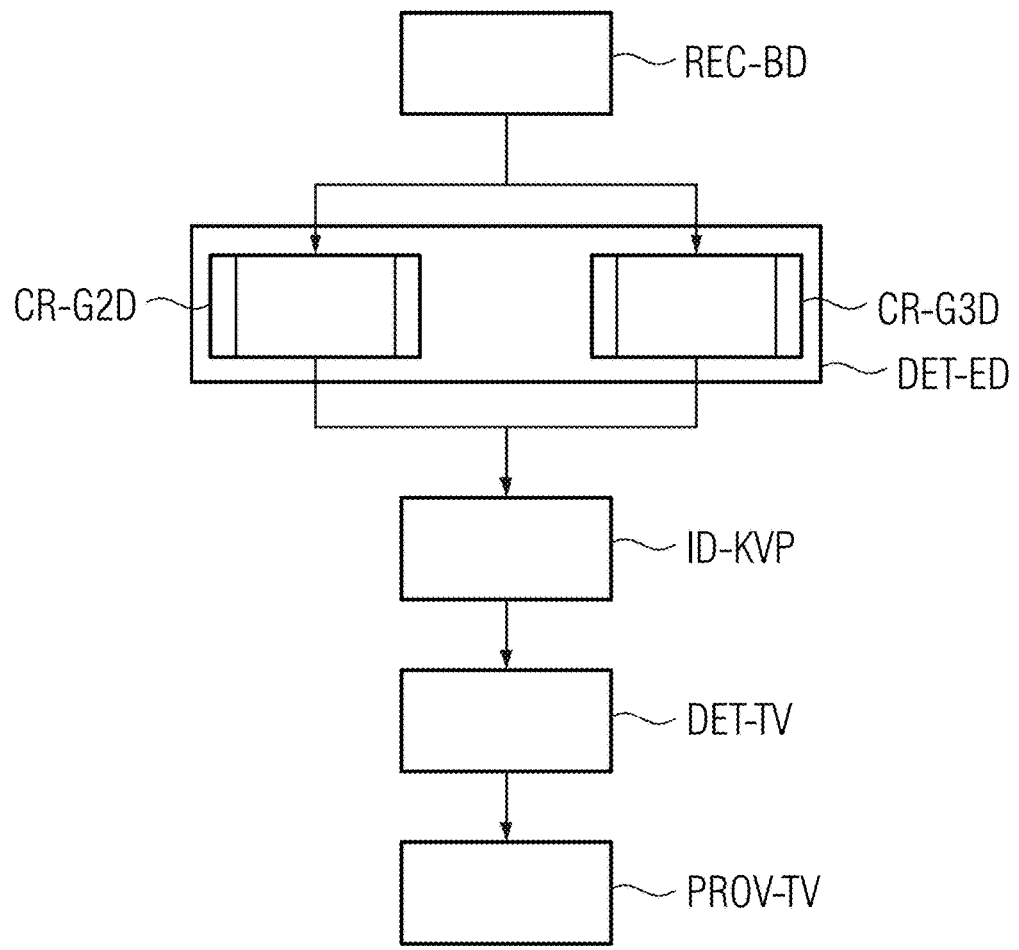

In the embodiment schematically illustrated in FIG. 6 of the proposed computer-implemented method for the provision of a transformation instruction TV, act b) may also include generation CR-G3D of the gradient image G3D from the 3D image B3D by application of the projection image G2. Furthermore, act b) may also include generation CR-G2D of the second gradient image G2D from the 2D image B2D.

Figure 7:
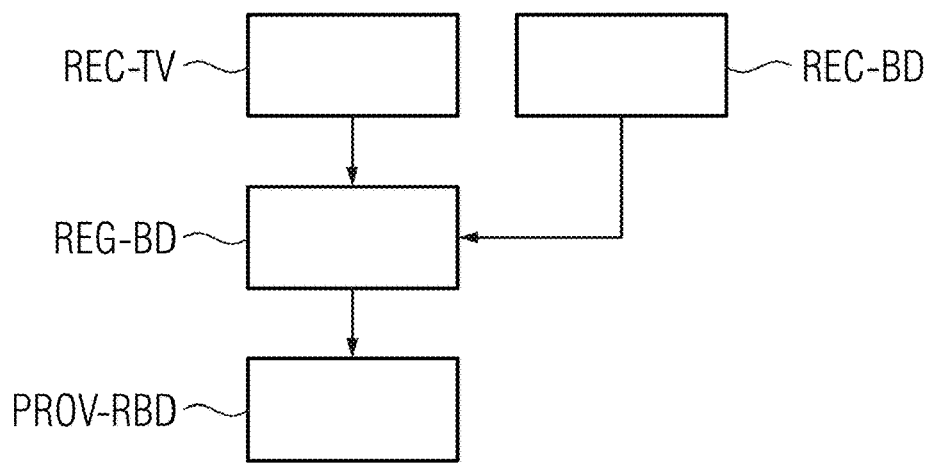
FIG. 7 depicts a schematic flowchart of an example of a computer-implemented method for registering a 2D image with a 3D image.
Figure 8:
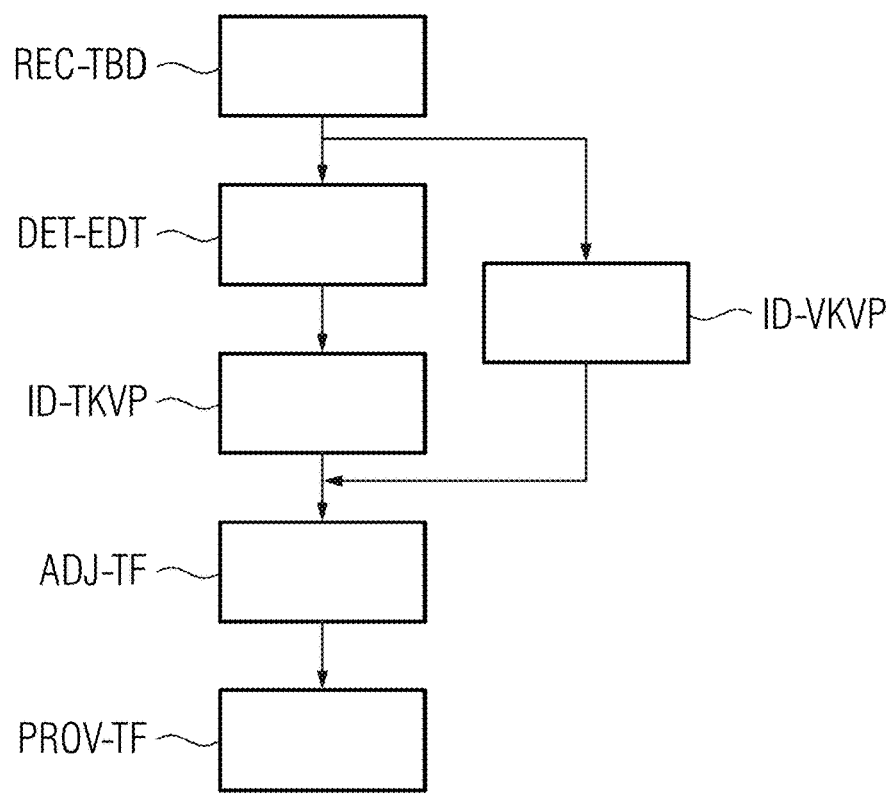
FIG. 8 depicts a schematic flowchart of an example of a computer-implemented method for the provision of a trained function.

FIG. 7 depicts a schematic flowchart of a computer-implemented method for registering a 2D image B2D with a 3D image B3D. A transformation instruction TV, the 2D image B2D, and the 3D image B3D may be received REC-TV and REC-BD in act r.a). The transformation instruction TV may be provided by a proposed computer-implemented method for the provision PROV-TV of a transformation instruction TV. The 2D image B2D may be registered REG-BD in act r.b) with the 3D image B3D based on the transformation instruction TV. In accordance with this the registered 3D image may be provided PROV-RBD in act r.c).

i) FIG. 8 depicts a schematic flowchart of a computer-implemented method for the provision of a trained function TF. A 2D training image and a 3D training image may be received REC-TBD in a first act t.a). Furthermore, comparison contour voxels of the 3D training image and comparison contour pixels of the 2D training image, which correspond with each other, may be identified ID-VKVP in act t.b). Identification may include the following acts: i) identification of contour features of the 3D training image, ii) identification of contour features of the 2D training image, iii) selection of the contour features of the 2D training image and the contour features of the 3D training image, which correspond with each other, iv) selection of the comparison contour pixels of the 2D training image and the comparison contour voxels of the 3D training image as a function of the contour features.

Input data may be generated DET-EDT in act t.c) based on the 2D training image including training contour pixels and the 3D training image including training contour voxels. The training contour pixels may be dependent on training contour features of the 2D training image. Furthermore, the training contour voxels may be dependent on training contour features of the 3D training image, which training contour voxels of the 3D training image have a substantially perpendicular contour surface normal in respect of a specified projection direction.

Furthermore, act t.c) may also include generation of a training gradient image from the 3D training image by applying a projection mapping. In addition, a second training gradient image may be generated in act t.c) from the 2D training image. The input data may also be based on the training gradient image and/or the second training gradient image.

In act t.d), the trained function may be applied to the input data for the identification ID-TKVP of training contour pixels of the 2D training image and training contour voxels of the 3D training image, which correspond with each other. Furthermore, at least one parameter of the trained function TF may be adjusted ADJ-TF in act t.e) based on a comparison of the training contour pixels with the comparison contour pixels and a comparison of training contour voxels corresponding thereto with the comparison contour voxels. In addition, the trained function TF may be provided PROV-TV in act t.f).

Furthermore, the 2D training image may include a projection image of an examination region depicted in the 3D training image. The projection direction may be specified in act t.c) as a function of the projection image.

In addition, act t.a) may also include receiving a training movement parameter. The contour features of the 2D training image may be adjusted in act t.b) and the training contour features of the 2D training image in act t.c) using the training movement parameter.

Figure 9:
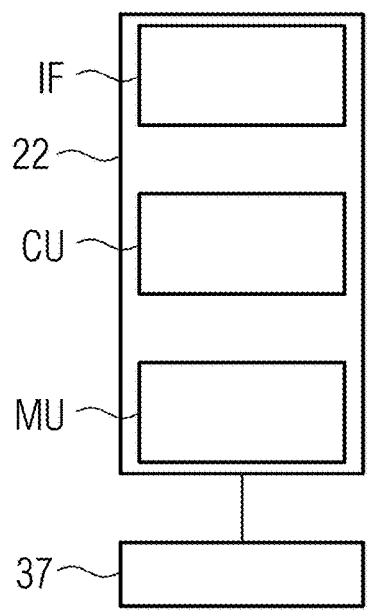
FIG. 9 depicts an exemplary embodiment of a processing unit.
Figure 10:
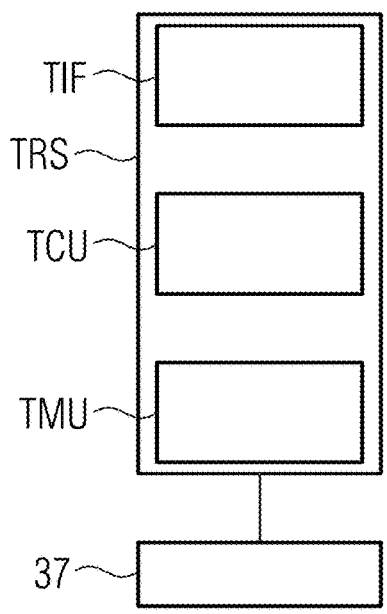
FIG. 10 depicts an exemplary embodiment of a training unit.

FIG. 9 depicts a processing unit 22, and FIG. 10 depicts a training unit TRS. Advantageously, the illustrated processing unit 22 may be designed to carry out an computer-implemented method for the provision PROV-TV of a transformation instruction TV for registering a 2D image B2D with a 3D image B3D. Advantageously, the illustrated training unit TRS may be designed to carry out a proposed computer-implemented method for the provision of a trained function TF. Advantageously, the processing unit 22 may include an interface IF, an arithmetic unit CU and a memory unit MU. Furthermore, the training unit TRS may advantageously include a training interface TIF, a training arithmetic unit TCU and a training memory unit TMU.

The interface IF may be designed for receiving REC-BD the 2D image B2D and the 3D image B3D. Furthermore, the arithmetic unit CU may be designed for generation DET-ED of input data ED based on the 2D image B2D including contour pixels KP and the 3D image B3D including contour voxels KV. The contour pixels KP may be dependent on contour features KM2D of the 2D image B2D. Furthermore, the contour voxels KV may be dependent on contour features KM3D of the 3D image B3D, which contour voxels KV of the 3D image B3D have a substantially perpendicular contour surface normal in respect of a specified projection direction. Furthermore, the arithmetic unit CU may be designed for application of a trained function TF to the input data ED for identification ID-KVP of contour pixels KP' of the 2D image B2D and contour voxels KV' of the 3D image B3D, which correspond with each other. At least one parameter of the trained function TF may be adjusted ADJ-TF to a comparison of training contour pixels with comparison contour pixels and a comparison of training contour voxels corresponding thereto with comparison contour voxels. Furthermore, the arithmetic unit CU may be designed for determining DET-TV a transformation instruction TV based on the identified contour pixels KP' of the 2D image B2D and the contour voxels KV' corresponding thereto of the 3D image B3D for registering REG-BD the 2D image B2D with the 3D image B3D. In addition, the interface IF may be designed for the provision PROV-TV of the transformation instruction TV. The transformation instruction TV may be provided PROV-TV, in particular, to a proposed medical imaging device 37.

Furthermore, the processing unit 22 may be designed to carry out a proposed computer-implemented method for registering REG-BD the 2D image B2D with the 3D image B3D.

Furthermore, the training interface TIF may be designed for receiving REC-TBD a 2D training image and a 3D training image. Furthermore, the training arithmetic unit TCU may be designed for identification ID-VKVP of comparison contour voxels of the 3D training image and comparison contour pixels of the 2D training image, which correspond with each other. Furthermore, the training arithmetic unit TCU may be designed for generation DET-EDT of input data based on the 2D training image including training contour pixels and the 3D training image including training contour voxels. Furthermore, the training arithmetic unit TCU may be designed for application of the trained function TF to the input data for identification ID-TKVP of training contour pixels of the 2D training image and training contour voxels of the 3D training image, which correspond with each other. In addition, the training arithmetic unit TCU may be designed for adjusting ADJ-TF at least one parameter of the trained function based on a comparison of the training contour pixels with the comparison contour pixels and a comparison of the training contour voxels corresponding thereto with the comparison contour voxels. Furthermore, the training interface TIF may be designed for the provision PROV-TF of the trained function. The trained function TF may be provided PROV-TF in particular to a proposed medical imaging device 37.

The processing unit 22 and/or the training unit TRS may be, in particular, a computer, a microcontroller or an integrated circuit. Alternatively, the processing unit 22 and/or the training unit TRS may be a real or virtual group of computers (a technical term for a real group is a "Cluster"; a technical term for a virtual group is "Cloud"). The processing unit 22 and/or the training unit TRS may also be designed as a virtual system, which is run on a real computer or a real or virtual group of computers (virtualization).

An interface IF and/or a training interface TIF may be a hardware or software interface (for example PCI bus, USB or Firewire). An arithmetic unit CU and/or a training arithmetic unit TCU may have hardware elements or software elements, for example, a microprocessor or what is known as an FPGA ("Field Programmable Gate Array"). A memory unit MU and/or a training memory unit TMU may be implemented as a non-permanent main memory (Random Access Memory, RAM for short) or as a permanent bulk memory (hard disk, USB stick, SD card, solid state disk).

The interface IF and/or the training interface TIF may include a plurality of sub-interfaces, which execute different acts of the respective method. In other words, the interface IF and/or the training interface TIF may also be understood as a large number of interfaces IF or large number of training interfaces TIF. The arithmetic unit CU and/or the training arithmetic unit TCU may include a plurality of sub-arithmetic units, which execute different acts of the respective method. In other words, the arithmetic unit CU and/or the training arithmetic unit TCU may also be understood as a large number of arithmetic units CU or large number of training arithmetic units TCU.

Figure 11:
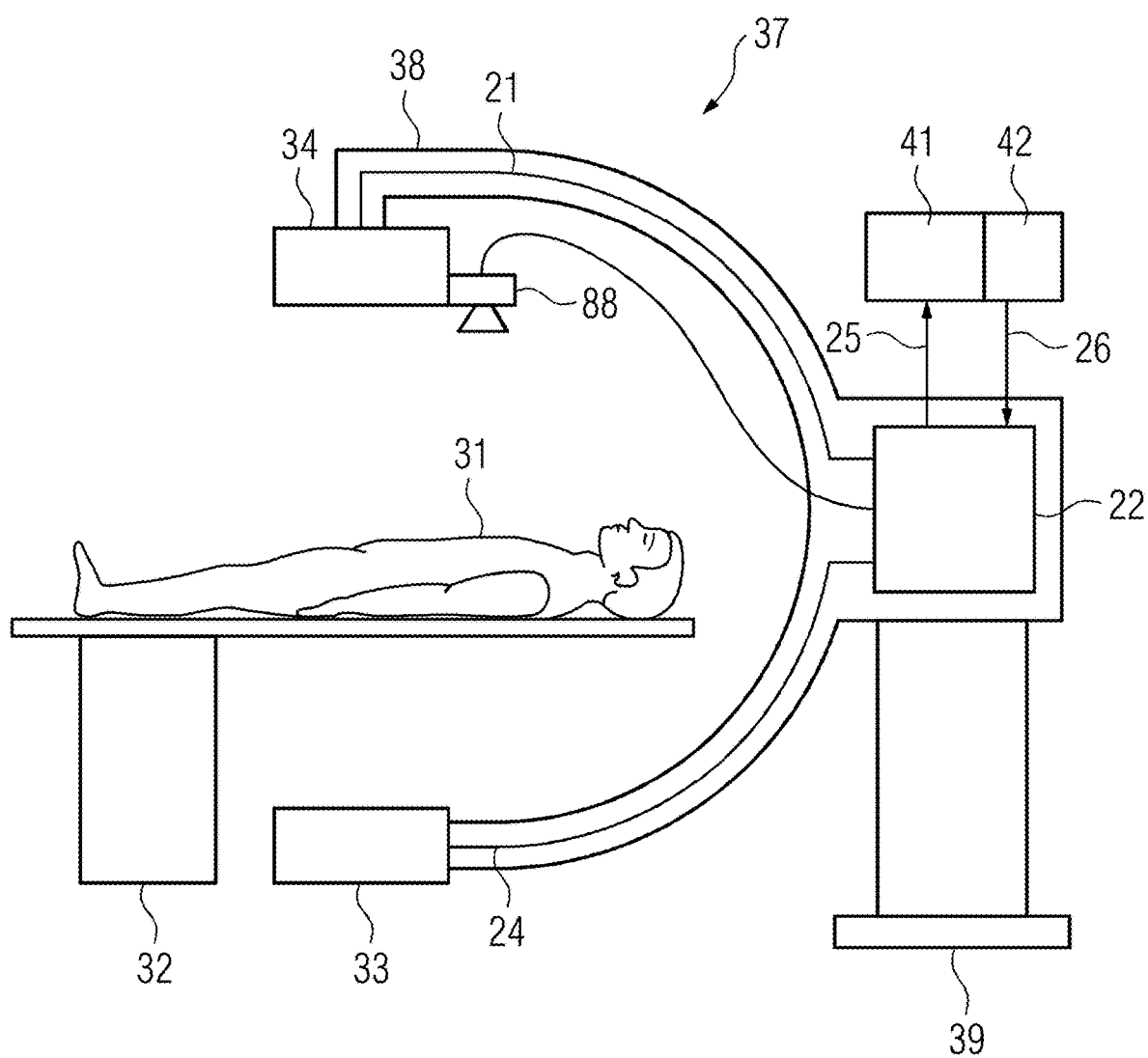
FIG. 11 depicts a schematic representation of an example of a proposed medical C-arm X-ray device.

FIG. 11 schematically illustrates an example of a proposed medical imaging device, a medical C-arm X-ray device 37. Advantageously, the medical C-arm X-ray device may be designed to carry out an embodiment of the proposed computer-implemented method for the provision PROV-TV of a transformation instruction TV for registering REG-BD a 2D image B2D with a 3D image B3D and/or a computer-implemented method for registering REG-BD a 2D image B2D with a 3D image B3D and/or a computer-implemented method for the provision PROV-TF of a trained function TF.

Here, the medical C-arm X-ray device 37 includes a detector unit 34, an X-ray source 33 and a processing unit 22. To record the 2D image B2D and/or the 3D image B3D, in particular at least one projection X-ray image, the arm 38 of the C-arm X-ray device may be supported so as to move around one or more axes. Furthermore, the medical C-arm X-ray device 37 may include a moving apparatus 39, enabling a movement of the C-arm X-ray device 37 in the space.

To record the 2D image B2D and/or the 3D image B3D of an examination region to be depicted of an examination object 31 arranged on a patient supporting apparatus 32, the processing unit 22 may send a signal 24 to the X-ray source 33. The X-ray source 33 may then emit an X-ray beam bundle, (e.g., a cone beam and/or fan beam). When the X-ray beam bundle strikes a surface of the detector unit 34, after an interaction with the region of the examination object 31 to be depicted, the detector unit 34 may send a signal 21 to the processing unit 22. The processing unit 22 may receive the 2D image B2D and/or the 3D image B3D, (e.g., using the signal 21).

Furthermore, the medical C-arm X-ray device 37 may include an input unit 41, such as a keyboard and/or a display unit 42, (e.g., a monitor and/or display). The input unit 41 may be integrated in the display unit 42, for example, in the case of a capacitive input display. An input by an operator at the input unit 41 makes it possible to control the proposed method and/or the medical C-arm X-ray device 37. For example, a graphic display of the 2D image B2D and/or the 3D image B3D and/or the gradient image G3D and/or the second gradient image G2D and/or at least one contour feature may be displayed on the display unit 42.

The medical C-arm X-ray device 37 may include a movement detection unit 88 which is designed to detect a movement and/or change in the examination region of the examination object 31. Advantageously, the movement detection unit may send a movement signal to the processing unit 22.

The schematic representations contained in the described figures do not indicate any sort of scale or proportion.

In conclusion, reference is made once again to the fact that the methods described in detail above and the illustrated apparatuses are merely exemplary embodiments which may be modified in a wide variety of ways by a person skilled in the art without departing from the scope of the disclosure. Furthermore, use of the indefinite article "a" or "an" does not preclude the relevant features from also being present several times. Similarly, the terms "unit" and "element" do not preclude the relevant components from including a plurality of cooperating sub-components, which, optionally, may also be spatially distributed.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A computer-implemented method for provision of a transformation instruction for registering a two-dimensional (2D) image with a three-dimensional (3D) image, the method comprising:
   receiving the 2D image and the 3D image;
   generating input data based on the 2D image comprising contour pixels and the 3D image comprising contour voxels, wherein the contour pixels are dependent on contour features of the 2D image, wherein the contour voxels are dependent on contour features of the 3D image, and wherein the contour voxels of the 3D image have a substantially perpendicular contour surface normal in respect of a specified projection direction;
   applying a trained function to the input data for identification of contour pixels of the 2D image and contour voxels of the 3D image, which correspond with each other, wherein at least one parameter of the trained function is adjusted based on a comparison of training contour pixels with comparison contour pixels and a comparison of training contour voxels corresponding thereto with comparison contour voxels; and
   determining the transformation instruction based on the identified contour pixels of the 2D image and the contour voxels corresponding thereto of the 3D image for registering the 2D image with the 3D image; and
   providing the transformation instruction.

2. The computer-implemented method of claim 1, wherein the 2D image comprises a projection image of an examination region of an examination object depicted in the 3D image, and
   wherein the specified projection direction is specified as a function of the projection image.

3. The computer-implemented method of claim 1, further comprising:
   adjusting the specified projection direction as a function of the transformation instruction; and
   repeating the generating of the input data, the applying of the trained function, the determining of the transformation instruction, and the adjusting of the specified projection direction until an occurrence of a termination condition.

4. The computer-implemented method of claim 1, wherein the generating of the input data further comprises creating a gradient image from the 3D image by applying a projection mapping, and
   wherein the input data is also based on the gradient image.

5. The computer-implemented method of claim 4, wherein the generating of the input data further comprises creating a second gradient image from the 2D image, and
   wherein the input data is also based on the second gradient image.

6. The computer-implemented method of claim 1, further comprising:
   receiving a movement parameter,
   wherein the contour features of the 2D image are adjusted in the generating of the input data using the movement parameter.

7. The computer-implemented method of claim 1, further comprising:
   registering the 2D image with the 3D image based on the transformation instruction; and
   providing the registered 3D image.

8. A computer-implemented method for provision of a trained function, the method comprising:
   receiving a two-dimensional (2D) training image and a three-dimensional (3D) training image;
   identifying comparison contour voxels of the 3D training image and comparison contour pixels of the 2D training image, which correspond with each other, by: identification of contour features of the 3D training image; identification of contour features of the 2D training image; selection of the contour features of the 2D training image and the contour features of the 3D training image, which correspond with each other; and selection of the comparison contour pixels of the 2D training image and the comparison contour voxels of the 3D training image as a function of the selected contour features of the 2D training image and the selected contour features of the 3D training image;
   generating input data based on the 2D training image comprising training contour pixels and the 3D training image comprising training contour voxels, wherein the training contour pixels are dependent on training contour features of the 2D training image, wherein the training contour voxels are dependent on training contour features of the 3D training image, which training contour voxels of the 3D training image have a substantially perpendicular contour surface normal in respect of a specified projection direction;
   applying the trained function to the input data for identification of training contour pixels of the 2D training image and training contour voxels of the 3D training image, which correspond with each other;
   adjusting at least one parameter of the trained function based on a comparison of the training contour pixel with the comparison contour pixels and a comparison of training contour voxels corresponding thereto with the comparison contour voxels; and
   providing the trained function.

9. The computer-implemented method of claim 8, wherein the 2D training image comprises a projection image of an examination region depicted in the 3D training image, wherein the specified projection direction is specified as a function of the projection image.

10. The computer-implemented method of claim 8, wherein the generating of the input data further comprises generation of a training gradient image from the 3D training image by applying a projection mapping, and
    wherein the input data is also based on the training gradient image.

11. A computer-implemented method of claim 10, wherein the generating of the input data further comprises generation of a second training gradient image from the 2D training image, and
    wherein the input data is also based on the second training gradient image.

12. The computer-implemented method of claim 8, further comprising:
    receiving a training movement parameter,
    wherein the contour features of the 2D training image and the training contour features of the 2D training image are adjusted using the training movement parameter.

13. A device for provision of a transformation instruction for registering a two-dimensional (2D) image with a three-dimensional (3D) image, the device comprising:
    a processor,
    wherein the processor is configured to receive the 2D image and the 3D image,
    wherein the processor is further configured to generate input data based on the 2D image comprising contour pixels and the 3D image comprising contour voxels, wherein the contour pixels are dependent on contour features of the 2D image, wherein the contour voxels are dependent on contour features of the 3D image, which contour voxels of the 3D image have a substantially perpendicular contour surface normal in respect of a specified projection direction,
    wherein the processor is further configured to apply a trained function to the input data for identification of contour pixels of the 2D image and contour voxels of the 3D image, which correspond with each other, wherein at least one parameter of the trained function is configured to be adjusted based on a comparison of training contour pixels with comparison contour pixels and a comparison of training contour voxels corresponding thereto with comparison contour voxels,
    wherein the processor is further configured to determine a transformation instruction based on the identified contour pixels of the 2D image and the contour voxels corresponding thereto of the 3D image for registering the 2D image with the 3D image, and
    wherein the processor is further configured to provide the transformation instruction.

14. The device of claim 13, wherein the device is a medical imaging device, and wherein the 2D image and the 3D image are images of an examination object.

15. A training unit for provision of a trained function, the training unit comprising:
    a training interface; and
    a training arithmetic unit, wherein the training interface is configured to receive a two-dimensional (2D) training image and a three-dimensional (3D) training image, wherein the training arithmetic unit is configured to identify comparison contour voxels of the 3D training image and comparison contour pixels of the 2D training image, which correspond with each other, by: identification of contour features of the 3D training image; identification of contour features of the 2D training image; selection of the contour features of the 2D training image and the contour features of the 3D training image, which correspond with each other; and selection of the comparison contour pixels of the 2D training image and the comparison contour voxels of the 3D training image as a function of the selected contour features of the 2D training image and the selected contour features of the 3D training image, wherein the training arithmetic unit is further configured to generate input data based on the 2D training image comprising training contour pixels and the 3D training image comprising training contour voxels, wherein the training contour pixels are dependent on training contour features of the 2D training image, wherein the training contour voxels are dependent on training contour features of the 3D training image, which training contour voxels of the 3D training image have a substantially perpendicular contour surface normal in respect of a specified projection direction, wherein the training arithmetic unit is further configured to apply the trained function to the input data for identification of training contour pixels of the 2D training image and training contour voxels of the 3D training image, which correspond with each other, wherein the training arithmetic unit is further configured to adjust at least one parameter of the trained function based on a comparison of the training contour pixels with the comparison contour pixels and a comparison of training contour voxels corresponding thereto with the comparison contour voxels, and wherein the training interface is further configured to provide the trained function.

* * * * *